[12] United States Patent  
Harper et al.

(10) Patent No.: US 7,067,555 B2  
(45) Date of Patent: Jun. 27, 2006

(54) SERTRALINE ORAL CONCENTRATE

(75) Inventors: Nancy J. Harper, Groton, CT (US); Gautam R. Ranade, East Lyme, CT (US); Willard M. Welch, Mystic, CT (US)

(73) Assignee: Pfizer Inc, New York, NY (US)

( * ) Notice: Subject to any disclaimer, the term of this patent is extended or adjusted under 35 U.S.C. 154(b) by 30 days.

(21) Appl. No.: 10/771,985

(22) Filed: Feb. 3, 2004

(65) Prior Publication Data

US 2004/0161434 A1    Aug. 19, 2004

Related U.S. Application Data

(63) Continuation of application No. 09/417,175, filed on Oct. 11, 1999, now Pat. No. 6,727,283.

(60) Provisional application No. 60/104,024, filed on Oct. 13, 1998.

(51) Int. Cl.  
  *A61K 31/185*  (2006.01)  
  *A61K 31/137*  (2006.01)  
  *C07C 39/04*   (2006.01)

(52) U.S. Cl. .................... 514/553; 514/649; 514/255; 514/555; 562/30; 564/308

(58) Field of Classification Search ............... 514/553, 514/649, 255, 555; 562/30; 564/308  
See application file for complete search history.

(56) References Cited

U.S. PATENT DOCUMENTS 4,962,128 A * 10/1990 Doogan et al. ............. 514/647  
5,597,826 A *  1/1997 Howard et al. ......... 514/252.14

FOREIGN PATENT DOCUMENTS

EP      0768083 A2 *  4/1997

* cited by examiner

*Primary Examiner*—Cecilia J. Tsang  
*Assistant Examiner*—Taylor Victor Oh  
(74) *Attorney, Agent, or Firm*—Steve T. Zelson; A. David Joran

(57) ABSTRACT

The present invention provides an essentially nonaqueous, liquid pharmaceutical concentrate composition for oral administration containing sertraline or a pharmaceutically acceptable salt thereof and one or more pharmaceutically acceptable excipients. The present invention also provides a use of this concentrate composition to prepare an aqueous solution of sertraline. In addition, the present invention provides a method of using this concentrate composition to treat or prevent a variety of diseases or conditions. Finally, the present invention provides the compound, (1S-cis)-4-(3, 4-dichlorophenyl)-1,2,3,4-tetrahydro-N-methyl-1-naphthalenamine methanesulfonate.

12 Claims, No Drawings

SERTRALINE ORAL CONCENTRATE

This application is a continuation of Ser. No. 09/417,175, filed Oct. 11, 1999 now U.S. Pat. No. 6,727,283, which claims the benefit of Ser. No. 60/104,024, filed Oct. 13, 1998.

FIELD OF THE INVENTION

The present invention provides an essentially nonaqueous, liquid pharmaceutical concentrate composition for oral administration containing sertraline or a pharmaceutically acceptable salt thereof and one or more pharmaceutically acceptable excipients. The present invention also provides a use of this concentrate composition to prepare an aqueous solution of sertraline. In addition, the present invention provides a method of using this concentrate composition to treat or prevent a variety of diseases or conditions. Finally, the present invention provides the compound, (1S-cis)-4-(3,4-dichlorophenyl)-1,2,3,4-tetrahydro-N-methyl-1-naphthalenamine methanesulfonate.

BACKGROUND OF THE INVENTION

Sertraline is a known compound having the following structure:

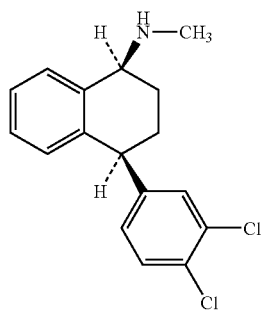

Sertraline has the following chemical name: (1S-cis)-4-(3,4-dichlorophenyl)-1,2,3,4-tetrahydro-N-methyl-1-naphthalenamine. Sertraline and its pharmaceutically acceptable acid addition salts, such as the hydrochloride salt, are disclosed in U.S. Pat. No. 4,536,518, which issued on 20 Aug. 1985, (hereafter referred to as the '518 patent), which is herein incorporated by reference in its entirety. Another pharmaceutically acceptable salt of sertraline is the mesylate salt.

The '518 patent states that sertraline and derivatives thereof are useful as antidepressant agents. U.S. Pat. No. 5,130,338, which issued on 14 Jul. 1992, refers to the use of sertraline to treat chemical dependencies, including dependencies on alcohol, tobacco and cocaine. U.S. Pat. No. 4,962,128, which issued on 9 Oct. 1990, refers to the use of sertraline to treat anxiety related disorders such as panic disorder, obsessive-compulsive disorder, generalized anxiety disorder, phobias, post traumatic stress disorder and avoidant personality disorder. U.S. Pat. No. 4,940,731, which issued on 10 Jul. 1990, refers to the use of sertraline to treat premature ejaculation. Published PCT patent application, WO 96/22085, which was published on 25 Jul. 1996, refers to the use of sertraline to treat cancer patients. Published European patent application 0768083, which published on 16 Apr. 1997, refers to the use of sertraline to treat post myocardial infarction patients.

U.S. Pat. No. 5,597,826, which issued on 28 Jan. 1997, relates to novel compositions containing a serotonin selective reuptake inhibitor (SSRI), such as sertraline, and an agonist or antagonist of the serotonin 1 (5-HT$_1$) receptor and to the use of such compositions for treating or preventing a condition selected from mood disorders, including depression, seasonal affective disorders and dysthmia, anxiety disorders, including generalized anxiety disorder and panic disorder; agoraphobia, avoidant personality disorder; social phobia; obsessive compulsive disorder; post-traumatic stress disorder; memory disorders including dementia, amnestic disorders and age-associated memory impairment; disorders of eating behavior, including anorexia nervosa and bulimia nervosa; obesity; cluster headache; migraine; pain; Alzheimer's disease; chronic paroxysmal hemicrania; headache associated with vascular disorders; Parkinson's disease, including dementia in Parkinson's disease, neuroleptic-induced parkinsonism and tardive dyskinesias; endocrine disorders such as hyperprolactinaemia; vasospasm (particularly in the cerebral vasculature); hypertension; disorders in the gastrointestinal tract where changes in motility and secretion are involved; sexual dysfunction, including premature ejaculation; and chemical dependencies. The foregoing published applications and U.S. patents are herein incorporated by reference in their entireties.

As noted above, sertraline hydrochloride is a selective serotonin reuptake inhibitor (SSRI) for oral administration. (Physicians' Desk Reference (PDR), 52nd ed., Supplement A, pages A250–A255 (1998).) Its mechanism, pharmacokinetics, and metabolism confer safety, once-daily dosage and efficacy in the treatment of depression, obsessive compulsive disorder and panic disorder. It is approved for the treatment of one or more of these indications in over 60 countries worldwide. The daily doses for sertraline, expressed as the free base, range from 50–200 mg, increasing in 50 mg increments. A titration dose of 25 mg/day during the initial phase of therapy may be warranted in some indications.

Tablet and capsule formulations of sertraline hydrochloride are commercially available in different countries. Capsular-shaped, scored tablets are available in strengths of 50 and 100 mg and are sold under the brand name, ZOLOFT® Tablets, in the U.S. The capsules are available in some countries in strengths of 50 mg and 100 mg.

The '518 patent discloses that sertraline and related compounds can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. According to this patent, when aqueous suspensions and/or elixirs are desired for oral administration, the essential active ingredient therein may be combined with various sweetening, or flavoring agents, coloring matter or dyes and, if so desired, emulsifying and/or suspending agents as well, together with such diluents as water, ethanol, propylene glycol, glycerin and various like combinations thereof.

However, development of an oral liquid dosage form of sertraline has been complicated by the objectionable bitter taste and astringency sensation imparted by the drug in liquid form. Thus, direct ("ready-to-use") oral liquid solutions or suspensions of sertraline, such as those described in the '518 patent above, have an objectionable taste, despite the inclusion of a variety of taste-masking or flavoring agents.

An oral liquid dosage form of sertraline with acceptable taste would be a valuable addition to the existing formulations, providing greater choice for both the prescriber and the patient. This is of importance with regard to the issue of non-compliance with treatment, which is believed to affect up to 50% of outpatients and appears to be a particular problem with elderly, pediatric and psychiatric patients (B. Blackwell, Drug Therapy: Patient Compliance, N.Engl. J.Med. 1973, 289(5):249–52). By virtue of being easier to swallow, an oral liquid dosage form of sertraline would offer an alternative to those patients who dislike or have difficulty swallowing tablets or capsules, and would therefore be of considerable benefit in treating those who may be non-compliant for those reasons. Therefore, there is a need in the art for an alternative liquid dosage form of sertraline that has acceptable taste and properties.

Oral concentrate drug products are known in the art and are commercially available. However, these concentrates are conventionally aqueous. For example, NAVANE® Concentrate contains the active ingredient, thiothixene hydrochloride, and the inert ingredients of alcohol, cherry flavor, dextrose, passion fruit flavor, sorbitol solution and water. (Physicians' Desk Reference (PDR), 52nd ed., pages 2192–2193 (1998).) SINEQUAN® Concentrate contains the active ingredient, doxepin hydrochloride, and the inert ingredients of glycerin, methylparaben, peppermint oil, propylparaben and water. (Physicians' Desk Reference (PDR), 52nd ed., pages 2203–2204 (1998).) TRILAFON® Concentrate contains the active ingredient, perphenazine, and the inert ingredients of alcohol, citric acid, flavors, menthol, sodium phosphate, sorbitol, sugar and water. (Physicians' Desk Reference (PDR), 52nd ed., pages 2666–2668 (1998)).

SUMMARY OF THE INVENTION

The present invention particularly provides:

A pharmaceutical composition which comprises:

an essentially nonaqueous, liquid concentrate for oral administration comprising an amount of sertraline or a pharmaceutically acceptable salt thereof and one or more essentially nonaqueous pharmaceutically acceptable excipients; wherein at least one of the excipients is liquid. Preferably, the pharmaceutically acceptable salts of sertraline are the hydrochloride salt and the mesylate salt.

More particularly, the present invention provides this composition wherein the concentrate contains sertraline hydrochloride, ethanol and glycerin. More specifically, in this concentrate, the sertraline hydrochloride is present in an amount of about 15 to about 30 mg/ml and the ethanol and glycerin are present at about 8 to about 20% ethanol (by weight) in glycerin.

The present invention also provides this composition wherein the concentrate contains sertraline hydrochloride, ethanol, glycerin and menthol. More specifically, in this concentrate, the sertraline hydrochloride is present in an amount of about 15 to about 30 mg/ml, the ethanol and glycerin are present at about 8 to about 20% ethanol (by weight) in glycerin, and the menthol is present in an amount of about 0.01 to about 5.0 mg/ml.

Most particularly, the present invention provides this composition wherein the concentrate contains sertraline hydrochloride, glycerin, ethanol, butylhydroxytoluene (BHT) and menthol. More specifically, each ml of this concentrate contains about 22.4 mg of sertraline hydrochloride, about 151 mg of ethanol, about 0.50 mg of menthol, about 0.10 mg of BHT, and a sufficient quantity of glycerin (which is about 1011 mg) to produce about 1 ml.

The present invention also provides the use of this essentially nonaqueous, liquid concentrate of sertraline or a pharmaceutically acceptable salt thereof to prepare an aqueous solution of sertraline which comprises: diluting the concentrate in an aqueous diluent prior to oral administration. Preferably, the pharmaceutically acceptable salts of sertraline are the hydrochloride salt and the mesylate salt.

The present invention also provides a method of treating or preventing diseases or conditions which are caused by disorders of the serotonergic system which comprises: a) diluting this concentrate in an aqueous diluent; and b) orally administering the resulting aqueous solution to a patient in need thereof. In addition, the present invention provides this method for treating or preventing diseases or conditions, such as the following: depression, anorexia, chemical dependencies, anxiety-related disorders (such as panic disorder, obsessive-compulsive disorder, generalized anxiety disorder, phobias, post traumatic stress disorder and avoidant personality disorder), premature ejaculation, cancer and post myocardial infarction.

The present invention also provides a process for making this essentially nonaqueous, liquid concentrate of sertraline or a pharmaceutically acceptable salt thereof.

Finally, the present invention provides the compound, (1S-cis)-4-(3,4-dichlorophenyl)-1,2,3,4-tetrahydro-N-methyl-1-naphthalenamine methanesulfonate.

DETAILED DESCRIPTION OF THE INVENTION

"Essentially nonaqueous" when used herein refers to the amount of water that is present in the final drug product, which amount is consistent with the amount of water potentially contributed by the active ingredient and/or by the excipients; however, no water is directly added to the final drug product. About 10% is the upper limit of the amount of water that may be present in the oral concentrate of the present invention. Typically, the amount of water that is present in the oral concentrate of the present invention ranges from about 0.8% to about 5.2% of the composition. Most typically, the amount of water that is present ranges from about 0.8% to about 2.0% of the composition.

"Concentrate" when used herein refers to a strong solution provided for dilution before use. (Butterworths Medical Dictionary, 2nd edition, Butterworths, London-Boston 1978, pp. 399–400.)

"Pharmaceutically acceptable excipient," as used herein, means a pharmacologically inactive ingredient which is used to formulate a drug product and which is readily known and available in the pharmaceutical arts. Examples of such excipients are given below.

"Pharmaceutically acceptable preservative," as used herein, means an additive or excipient that preserves the quality of the formulation from a chemical or microbiological standpoint. Examples of preservatives are given below.

"Serotonergic system" when used herein refers to the neuronal process whereby serotonin is released by a pre-synaptic cell upon excitation and crosses the synapse to stimulate or inhibit the post-synaptic cell.

The sertraline oral concentrate of the present invention is a new dosage form of sertraline intended as a multidose product for oral use only. The oral concentrate is an essentially non-aqueous, optionally flavored solution of sertraline, preferably as the hydrochloride salt, which is intended to be diluted prior to administration.

The oral concentrate of the present invention is advantageous because, inter alia, it provides convenience in measuring different doses, which are needed for certain indications, and acceptable taste upon administration, as well as good physical/chemical stability characteristics throughout the product's shelf-life and use interval. Also, since the concentrate of the present invention is a solution, it is preferred over a suspension for ease of manufacture and optimal control of dosing homogeneity.

The active ingredient in the concentrate of the present invention is sertraline, which may be present as its free base or as its pharmaceutically acceptable salt. Such salts include, for example, the hydrochloride salt and the methanesulfonate salt (also known as the mesylate salt). In the concentrate of the present invention, the hydrochloride salt is preferred.

The preparation of sertraline and its hydrochloride salt is described in the '518 patent referenced above, particularly in Example 2 of that patent. The mesylate salt is prepared by reacting the sertraline free base with methanesulfonic acid at room temperature in a solvent, such as ethyl acetate, methanol, ethanol and isopropanol. The mesylate salt has favorable properties, such as solubility in polar vehicles and good chemical stability.

Sertraline hydrochloride may be present in the concentrate of the present invention in an amount of about 1 mg/ml up to about 88 mg/ml of the composition. Preferably, it is present in an amount of about 15 to about 30 mg/ml of the composition. Most preferably, about 20 mg sertraline per ml, which is equivalent to about 22.4 mg/ml as the hydrochloride (assuming a theoretical stoichiometric potency of 89.4%), is present. The quantity of sertraline hydrochloride needed to produce a concentration of about 20 mg sertraline per ml is adjusted based on the actual potency of the drug substance lot to be used.

One or more pharmaceutically acceptable excipients are present in the concentrate of the present invention. Examples of such excipients include the following: ethanol, glycerin (also referred to as glycerol or glycerine), propylene glycol and polyethylene glycols. All of these excipients are well known in the pharmaceutical arts and are commercially available.

From among these excipients, binary combinations of ethanol and glycerin provide maximum solubilization of the sertraline hydrochloride drug substance and are preferred. In these combinations, the amount of ethanol that is present is about 8% to about 50% (w/w) in glycerin; preferably, about 8 to about 20% (w/w) ethanol in glycerin is present; most preferably, about 10 to about 14% (w/w) ethanol in glycerin is present. The ethanol that may be used in the concentrate of the present invention is any compendial grade of ethanol, including ethanol (95%) and anhydrous ethanol.

The concentrate of the present invention optionally contains one or more flavoring agents or taste-masking flavors. Examples of candy-type flavoring agents include mint, citrus and fruit flavoring agents. The mint flavoring agents, such as peppermint, spearmint and menthol (also referred to as levomenthol), are preferred. More specifically, from among a variety of mint flavoring agents, menthol is preferred and may be present in an amount of about 0.01 to about 5.0 mg/ml of the composition; preferably, menthol is present in an amount of about 0.5 mg/ml of the composition.

The concentrate of the present invention also optionally contains one or more pharmaceutically acceptable preservatives, which preserve the quality of the concentrate from a chemical or microbiological standpoint. Preservatives, such as antioxidants, metal chelators, metal complexing agents and antimicrobial agents, may be used in the concentrate of the present invention. These preservatives may be used in the concentrate, both alone and in various combinations (e.g., antioxidant(s) in combination with a metal complexing agent), to improve product stability. When the concentrate of the present invention contains ethanol, it may be appropriately microbiologically self-preserved.

Examples of preservatives, which may be present in the concentrate of the present invention, include the following: butylhydroxytoluene (BHT, also referrred to as butylated hydroxytoluene), butylated hydroxyanisole (BHA), propyl gallate, ascorbic acid, ascorbyl palmitate, sodium metabisulite, sodium bisulfite, sodium thiosulfate, sodium hydroxide, cystiene, ethylenediamine tetraacetic acid (EDTA) or its salts (such as the sodium salt), citric acid, triethanolamine, thioglycerol, methylparaben and propylparaben. Also, various combinations of these preservatives may be present in the concentrate of the present invention, such as the following: disodium EDTA and BHA; disodium EDTA, BHA and BHT; disodium EDTA and propyl gallate; and BHA and BHT.

The amount of preservative that may be present in the concentrate of the present invention ranges from about 0.01 to about 10.0 mg/ml of the composition. In the concentrate of the present invention, butylhydroxytoluene (BHT) is preferred and may be present in an amount of about 0.01 to about 0.5 mg/ml of the composition; preferably, it is present in an amount of about 0.01 to about 0.2 mg/ml of the composition; more preferably, it is present in amount of about 0.01 to about 0.13 mg/ml of the composition; most preferably, it is present in an amount of about 0.05 to about 0.11 mg/ml of the composition.

The sertraline oral concentrate of the present invention is intended to be diluted in a suitable diluent or beverage prior to administration. For example, doses of the oral concentrate (equivalent to about 25 mg and about 200 mg of sertraline) are mixed with approximately 4 oz. (about 120 ml or ½ cup) of a suitable diluent or beverage. The following beverages may be used for the preparation and administration of the dose: water, orange juice, ginger ale, lemon-lime soda, lemonade, sugared tap water, cranberry juice, grapefruit juice, tomato juice, pineapple juice, prune juice, orange drink and Gatorade® (beverage, not powder). Water, orange juice, ginger ale, lemon-lime soda and lemonade are preferred. The proper dose of sertraline oral concentrate may be most conveniently added to these beverages by means of a dropper calibrated at, for example, 25 and 50 mg (as sertraline).

The manufacture of sertraline oral concentrate utilizes conventional pharmaceutical equipment and processes. For example, the manufacturing process for sertraline hydrochloride oral concentrate involves dissolving the sertraline hydrochloride drug substance in a solution of glycerin, ethanol, and optionally other excipients, such as butylhydroxytoluene (BHT) and menthol, followed by clarifying filtration, if desired, and filling into containers such as bottles, as appropriate.

Preferably, to facilitate BHT incorporation, this component is first dissolved in a portion of the ethanol, which is then added to the main compounding tank containing the glycerin and the remainder of the ethanol. Menthol and sertraline hydrochloride are then sequentially added and mixed to dissolve. The sertraline hydrochloride is intentionally added to the solution last to optimize the protective effect of the antioxidant (BHT). The compounded solution is passed through a filter, and the final product is filled into appropriate containers, such as bottles. The final product may be supplied in a variety of presentations, such as a 60 ml presentation, which is packaged in, for example, a 60 ml, amber glass bottle with a child-resistant closure.

EXAMPLES

Example 1

Concentrate solution (20 mg sertraline/ml) with preservative and menthol flavoring:

| Ingredients | mg/ml | % w/v (g/100 ml) | mg/60 ml |
|---|---|---|---|
| Sertraline HCl | 22.37 | 2.237 | 1342.3 |
| Ethanol (95%) | 150.68 | 15.068 | 9040.8 |
| Menthol | 0.50 | 0.050 | 30.0 |
| BHT | 0.10 | 0.010 | 6.0 |
| Glycerin | 1010.81 | 101.081 | 60648.6 |
| Total | 1184.46 | 118.446 | 71067.7 |

BHT, menthol and drug were dissolved in a mixture of glycerin and ethanol. The resulting mixture may be blanketed with nitrogen due to the ethanol content and associated potential flammability. The resulting mixture may be filtered, if desired.

Example 2

One ml of a nonaqueous solution containing 1–23 mg sertraline HCl/ml:
Sertraline Hydrochloride: 1–23 mg
Polyethylene glycol 300 (PEG-300): sufficient quantity to produce 1 ml
Dissolve the drug substance in the PEG with stirring.

Example 3

One ml of a nonaqueous solution containing 1–64 mg sertraline HCl/ml:
Sertraline Hydrochloride: 1–64 mg
Propylene Glycol: sufficient quantity to produce 1 ml
Dissolve the drug substance in the propylene glycol with stirring.

Example 4

One ml of a nonaqueous solution containing 1–17 mg sertraline HCl/ml:
Sertraline Hydrochloride: 1–17 mg
Ethanol: sufficient quantity to produce 1 ml
Dissolve the drug substance in the ethanol with stirring.

Example 5

One ml of a nonaqueous solution containing 1–78 mg sertraline HCl/ml:
Sertraline Hydrochloride: 1–78 mg
Ethanol: 100–500 mg
Glycerin: sufficient quantity to produce 1 ml
Dissolve the drug substance in a mixture of ethanol and glycerin with stirring.

Example 6

1000 ml concentrate solution (20 mg sertraline/ml) with peppermint flavoring:
Sertraline HCl: 22.4 g
Ethanol (95%): 127 g
Natural Peppermint Stick flavoring: 0.01–1.7 g
Glycerin: 852–872 g or sufficient quantity to produce 1000 ml
Dissolve the natural peppermint stick flavoring and drug in a mixture of ethanol and glycerin.

Example 7

1000 ml concentrate solution (20 mg sertraline/ml) with menthol flavoring:
Sertraline HCl: 22.4 g
Ethanol (95%): 127 g
Menthol: 0.01–1.7 g
Glycerin: 852–872 g or sufficient quantity to produce 1000 ml
Dissolve the menthol and drug in a mixture of ethanol and glycerin.

Example 8

1000 ml concentrate solution (20 mg sertraline/ml) with preservatives and peppermint flavoring:
Sertraline HCl: 22.4 g
Ethanol, anhydrous: 127 g
Natural Peppermint Stick flavoring: 1.7 g
Methylparaben: 0.6 g
Propylparaben: 0.3 g
Glycerin: 852–872 g or sufficient quantity to produce 1000 ml
The natural peppermint stick flavoring, parabens and drug were dissolved in a mixture of ethanol/glycerin.

Example 9

1000 ml concentrate solution (20 mg sertraline/ml) with preservatives and no flavoring:
Sertraline HCl: 22.4 g
Ethanol, anhydrous: 127 g
Methylparaben: 0.6 g
Propylparaben: 0.3 g
Glycerin: 852–872 g or sufficient quantity to produce 1000 ml
The parabens and drug were dissolved in a mixture of ethanol/glycerin.

Examples 10–30

The following examples describe various 1000 ml concentrate solutions of sertraline hydrochloride (20 mg sertraline/ml) with preservatives and menthol flavoring:

Example 10

Sertraline HCl: 22.7 g
Ethanol, 95%: 151.0 g
Menthol: 0.5 g
Citric acid: 0.1 g
Glycerin: 1010.7 g or sufficient quantity to produce 1000 ml

Example 11

Sertraline HCl: 22.7 g
Ethanol, 95%: 151.0 g
Menthol: 0.5 g
Propyl gallate: 0.1 g
Glycerin: 1010.7 g or sufficient quantity to produce 1000 ml

Example 12

Sertraline HCl: 22.7 g
Ethanol, 95%: 151.0 g
Menthol: 0.5 g
BHA: 0.1 g
Glycerin: 1010.7 g or sufficient quantity to produce 1000 ml

Example 13

Sertraline HCl: 22.7 g
Ethanol, 95%: 151.0 g
Menthol: 0.5 g
Sodium metabisulfite: 0.5 g
Glycerin: 1010.7 g or sufficient quantity to produce 1000 ml

Example 14

Sertraline HCl: 22.7 g
Ethanol, 95%: 151.0 g
Menthol: 0.5 g
Ascorbyl palmitate: 0.1 g
Glycerin: 1010.7 g or sufficient quantity to produce 1000 ml

Example 15

Sertraline HCl: 22.7 g
Ethanol, 95%: 151.0 g
Menthol: 0.5 g
Sodium bisulfite: 0.5 g
Glycerin: 1010.7 g or sufficient quantity to produce 1000 ml

Example 16

Sertraline HCl: 22.7g
Ethanol, 95%: 151.0 g
Menthol: 0.5 g
Triethanolamine: 0.1–0.5 g
Glycerin: 1010.7g or sufficient quantity to produce 1000 ml

Example 17

Sertraline HCl: 22.7 g
Ethanol, 95%: 151.0 g
Menthol: 0.5 g
BHT: 0.1 g
Glycerin: 1010.7 g or sufficient quantity to produce 1000 ml

Example 18

Sertraline HCl: 22.7 g
Ethanol, 95%: 151.0 g
Menthol: 0.5 g
1 N sodium hydroxide: 0.03 g
Glycerin: 1010.7 g or sufficient quantity to produce 1000 ml

Example 19

Sertraline HCl: 22.7 g
Ethanol, 95%: 151.0 g
Menthol: 0.5 g
Disodium EDTA: 0.1 g
Glycerin: 1010.7 g or sufficient quantity to produce 1000 ml

Example 20

Sertraline HCl: 22.7 g
Ethanol, 95%: 151.0 g
Menthol: 0.5 g
Ascorbic acid: 0.1 g
Glycerin: 1010.7 g or sufficient quantity to produce 1000 ml

Example 21

Sertraline HCl: 22.7 g
Ethanol, 95%: 151.0 g
Menthol: 0.5 g
Thioglycerol: 1.0 g
Glycerin: 1010.7 g or sufficient quantity to produce 1000 ml

Example 22

Sertraline HCl: 22.7 g
Ethanol, 95%: 151.0 g
Menthol: 0.5 g
Sodium thiosulfate: 0.5 g
Glycerin: 1010.7 g or sufficient quantity to produce 1000 ml

Example 23

Sertraline HCl: 22.7 g
Ethanol, 95%: 151.0 g
Menthol: 0.5 g
BHT: 0.1 g
BHA: 0.1 g
Glycerin: 1010.7 g or sufficient quantity to produce 1000 ml

Example 24

Sertraline HCl: 22.7 g
Ethanol, 95%: 151.0 g
Menthol: 0.5 g
BHT: 0.1 g
BHA: 0.1 g
Citric acid: 0.1 g
Glycerin: 1010.7 g or sufficient quantity to produce 1000 ml

Example 25

Sertraline HCl: 22.7 g
Ethanol, 95%: 151.0 g
Menthol: 0.5 g
BHT: 0.1 g
BHA: 0.1 g
Propyl gallate: 0.1 g
Glycerin: 1010.7 g or sufficient quantity to produce 1000 ml

Example 26

Sertraline HCl: 22.7 g
Ethanol, 95%: 151.0 g
Menthol: 0.5 g
Disodium EDTA: 0.1 g
Sodium metabisulfite: 0.5 g
Glycerin: 1010.7 g or sufficient quantity to produce 1000 ml

Example 27

Sertraline HCl: 22.7 g
Ethanol, 95%: 151.0 g
Menthol: 0.5 g
Cystiene: 1.0 g
Glycerin: 1010.7 g or sufficient quantity to produce 1000 ml

Example 28

Sertraline HCl: 22.7 g
Ethanol, 95%: 151.0 g
Menthol: 0.5 g
BHT: 0.1 g
BHA: 0.1 g
Triethanolamine: 0.1–0.5 g
Glycerin: 1010.7g or sufficient quantity to produce 1000 ml

Example 29

Sertraline HCl: 22.7 g
Ethanol, 95%: 151.0 g
Menthol: 0.5 g
Disodium EDTA: 0.1 g
BHT: 0.1 g
BHA: 0.1 g
Glycerin: 1010.7 g or sufficient quantity to produce 1000 ml

Example 30

Sertraline HCl: 22.7 g
Ethanol, 95%: 151.0 g
Menthol: 0.5 g
Disodium EDTA: 0.1 g
BHA: 0.1 g
Glycerin: 1010.7 g or sufficient quantity to produce 1000 ml For Examples 10–30 above, the menthol and preservative were dissolved in ethanol.
Glycerin was added and dispersed. The drug was added and dissolved.

The invention claimed is:

1. A pharmaceutical composition which comprises:
an essentially nonaqueous, liquid concentrate solution for oral administration comprising an amount of sertraline or a pharmaceutically acceptable salt thereof and one or more essentially nonaqueous pharmaceutically acceptable excipients; wherein at least one of the excipients is liquid, and wherein the excipients are selected from the group consisting of ethanol, glycerin, polyethylene glycol and propylene glycols, and wherein the concentrate comprises sertraline in an amount of about 1 to about 88 mg/ml.

2. The composition of claim 1 wherein the pharmaceutically acceptable salt of sertraline is the hydrochloride salt or the mesylate salt.

3. The composition of claim 1 wherein the excipients are ethanol and glycerin.

4. The composition of claim 1 wherein the concentrate comprises sertraline hydrochloride in an amount of about 15 to about 30 mg/ml and wherein the excipients are ethanol and glycerin in an amount of about 8 to about 20% ethanol (by weight) in glycerin.

5. The composition of claim 4 wherein the concentrate further comprises one or more flavoring agents and one or more pharmaceutically acceptable preservatives.

6. The composition of claim 5 wherein the flavoring agents are selected from the group consisting of peppermint, spearmint and menthol; and wherein the preservatives are selected from the group consisting of butylhydroxytoluene, butylated hydroxyanisole, propyl gallate, ascorbic acid, ascorbyl palmitate, sodium metabisulfite, sodium bisulfite, sodium thiosulfate, sodium hydroxide, cysteine, ethylenediamine tetraacetic acid or salts thereof, citric add, triethanolamine, thioglycerol, methylparaben and propylparaben.

7. The composition of claim 6 wherein the flavoring agent is menthol and wherein the preservative is butylhydroxytoluene.

8. The composition of claim 7 wherein each ml of the concentrate comprises about 22.4 mg of sertraline hydrochloride, about 151 mg of ethanol, about 0.50 mg of menthol, about 0.10mg of butylhydroxytoluene, and about 1011 mg of glycerin.

9. The compound, (1S-cis)-4-(3,4-dichlorophenyl)-1,2,3,4-tetrahydro-N-methyl-1-naphthalenamine methanesulfonate.

10. A method of preparing an aqueous solution of sertraline comprising diluting an essentially nonaqueous, liquid concentrate of sertraline according to claim 1, or a pharmaceutically acceptable salt thereof, in an aqueous diluent prior to oral administration, said concentrate comprising an amount of sertraline or a pharmaceutically acceptable salt thereof and one or more essentially nonaqueous pharmaceutically acceptable excipients, wherein at least one of the excipients is liquid, and wherein the excipients are selected from the group consisting of ethanol, glycerin, polyethylene glycol and propylene glycols, and wherein the concentrate comprises sertraline in an amount of about 1 to about 88 mg/ml.

11. The method of claim 10, wherein the pharmaceutically acceptable salt of sertraline is the hydrochloride salt or the mesylate salt.

12. The method of claim 11 wherein the diluent is selected from the group consisting of water, orange juice, ginger ale, lemon-lime soda and lemonade.

* * * * *